United States Patent [19]

Fong et al.

[11] Patent Number: 4,802,992

[45] Date of Patent: * Feb. 7, 1989

[54] REMOVAL OF DISPERSED OIL FROM WATER

[75] Inventors: Dodd W. Fong, Naperville; Ann M. Halverson, Wheaton, both of Ill.

[73] Assignee: Nalco Chemical Company, Naperville, Ill.

[ * ] Notice: The portion of the term of this patent subsequent to Aug. 5, 2003 has been disclaimed.

[21] Appl. No.: 58,826

[22] Filed: Jun. 5, 1987

Related U.S. Application Data

[62] Division of Ser. No. 740,436, Jun. 3, 1985, abandoned.

[51] Int. Cl.$^4$ ............................................. B01D 17/05
[52] U.S. Cl. ..................................... 210/709; 210/734; 210/735; 526/263
[58] Field of Search ........................ 210/709, 734, 735

[56] References Cited

U.S. PATENT DOCUMENTS 4,515,658 5/1985 Fong ................................ 162/168.4
4,604,213 8/1986 Fong .................................. 210/735

*Primary Examiner*—Christopher Henderson
*Attorney, Agent, or Firm*—Joan I. Norek; John G. Premo; Donald G. Epple

[57] ABSTRACT

The present invention provides the methyl chloride and dimethyl surfate quaternary ammonium salts of 1-acryloyl-4-methyl piperazine, their homopolymers and copolymers, and water clarification processes in which is used polymers of 1-acryloyl-4-methyl piperazine.

3 Claims, No Drawings

REMOVAL OF DISPERSED OIL FROM WATER

This is a division of application Ser. No. 740,436 filed on June 3, 1985, now abandoned.

TECHNICAL FIELD OF THE INVENTION

The present invention is in the technical field of vinyl addition monomers, polymers derived therefrom, and emulsion breaking applications in which such polymers are useful.

BACKGROUND OF THE INVENTION

Many industries have need for materials having emulsion breaking activity, such as materials active in causing the resolution of an oil-in-water emulsion into separate continuous oil and water phases. Such industries include the oil production industry where waters from the oil fields contain undesirable oil dispersed therein, and in this instance undesirable solids. Other examples are the pulping and paper producing industries, the metal and automotive industries.

New materials having activity in emulsion breaking, or emulsion resolution, applications and processes are highly desired and sought. Not only are active materials of greater efficiencies than those presently available desirable, but also active materials of different chemical compositions in and of themselves, to augment the available selection of materials and widen the choices for any given need. This latter aspect, the widening of choices per se, is particularly important in such emulsion breaking and oily water clarification applications where environmental conditions influencing the process can vary significantly.

DISCLOSURE OF THE INVENTION

The present invention provides new vinyl addition monomers, i.e., the methyl chloride and dimethyl sulfate quaternary ammonium salts of 1-acryloyl-4-meyhyl piperazine and polymers that are derived therefrom.

Such polymers include homopolymers of the quaternary ammonium salts of 1-acryloyl-4-methyl piperazine or polymeric compositions comprising one or more other vinyl addition monomers polymerized together with such quaternary ammonium salt. Such other vinyl addition monomers must have reactivity ratios suitable for polymerizing with the 1-acryloyl-4-methyl piperazine quaternary ammonium salts of the present invention. A particularly useful monomer for such polymerization is acrylamide.

The other vinyl addition monomers that may be incorporated into the polymers of the present invention may be either water-soluble or water-insoluble. They may be nonionic, cationic, or anionic, or combinations thereof. The polymers may themselves be water-soluble, such as the homopolymers of the 1-acryloyl-4-methyl piperazine quaternary ammonium salts, or water-insoluble. These polymers may be prepared using conventional solution polymerization techniques or methods in which water-soluble vinyl addition monomers are polymerized in the form of water-in-oil emulsions.

The present invention also provides water clarification processes in which the active agent, or at least one of the active agents, is a polymeric product of the polymerization of the vinyl addition monomer 1-acryloyl-4-methyl piperazine or its quaternary ammonium salt, either as homopolymers or together with other vinyl addition monomers capable of polymerization therewith, as described in more detail below.

PREFERRED EMBODIMENTS OF THE INVENTION

The novel vinyl addition monomers of the present invention, the methyl chloride and dimethyl sulfate quaternary ammonium salts of 1-acryloyl-4-methyl piperazine, can be prepared from 1-acryloyl-4-methyl piperazine and, respectively, methyl chloride or dimethyl sulfate. Such a synthesis and the preparation of the 1-acryloyl-4-methyl piperazine itself are described below in Examples 1, 2, and 3.

EXAMPLES 1 AND 2

164.47 grams of dimethyl sulfate were added slowly to 196.4 grams of 1-acryloyl-4-methyl piperazine in 354.86 grams of water with cooling, and then the reaction mixture was stirred for 2 hours at room temperature. The material was stabilized with methyl hydroquinone and the solution's pH was raised above 3 with caustic. The product was characterized by C13 NMR.

Into a 300 ml. Parr bomb was charged 26.6 grams water, 21 grams 1-acryloyl-4-methyl piperaine, and 10 grams methyl chloride. The valves were closed and the bomb was heated to and maintained at 60° C. until no more methyl chloride was taken up. The product was characterized by C13 NMR.

EXAMPLE 3

Acryloyl chloride (102 g.) in methylene chloride (100 ml.) was added into a methylene chloride (450 ml.) solution of N-methyl piperazine (86 g.) over a period of one hour. The reaction temperature was kept below 25° C. with cooling. After the addition was completed, the reaction mixture was stirred at ambient temperature for two hours. Then 260 g. of a 17% sodium carbonate in water solution was added with stirring. A crude product of 1-acryloyl-4-methyl piperazine (100 g.) was recovered from the methylene chloride solution and distilled. The fraction recovered at 74°–78° C./5 mm Hg was characterized by C13 NMR.

The 1-acryloyl-4-methyl piperazine and its quaternary ammonium salt are both water-soluble vinyl addition monomers, the first being nonionic and the latter cationic.

For polymerization together with the quaternary ammonium salts of 1-acryloyl-4-methyl piperazine, suitable nonionic monomers include: acrylamide, methacrylamide, acrylonitrile, N-vinyl pyrrolidinone, vinyl acetate, lower alkyl acrylates, lower alkyl methacrylates, lower alkyl ethacrylates, styrene and the like. Suitable cationic monomers include: dimethylaminoethylacrylate, quaternary ammonium salts of dimethylaminoethylacrylate, dimethylaminoethylmethacrylate, quaternary ammonium salts of dimethylaminoethylmethacrylate, diallyldimethylammonium chloride, methacrylamidopropyltrimethylammonium chloride, vinyl pyridine, N,N-dimethylaminomethylacrylamide, N,N-dimethylaminomethylmethacrylamide, N,N-dimethylaminomethylacrylamide quaternary ammonium salts, and the like. Suitable anionic monomers include: acrylic acid, methacrylic acid, itaconic acid, maleic anhydride, acrylamidomethylpropanesulfonic acid, and the like.

When the quaternary ammonium salt(s) of 1-acryloyl-4-methyl piperazine is polymerized together with other vinyl addition monomers, the resultant polymeric composition may contain from about 1 to about 99 mole percent of the other vinyl addition co-monomer or co-monomers. In preferred embodiment, such polymeric compositions will contain from about 1 to about 70 mole percent, and more preferably from about 2 to about 50 mole percent, of the other vinyl addition co-monomer or co-monomers.

Particularly useful novel polymers of the present invention are those derived from the polymerization of the 1-acryloyl-4-methyl piperazine quaternary ammonium salt together with acrylamide. Such copolymers, like the homopolymers of such quaternary ammonium salts, have been found extremely active in water clarification and emulsion resolution processes. Such polymeric compositions may contain from about 1 to about 99 mole percent of acrylamide. In preferred embodiment, such polymeric compositions contain from about 50 to about 95 mole percent acrylamide, and more preferably from about 65 to about 95 mole percent acrylamide. Such polymers, of course, may contain other vinyl addition co-monomers in addition to the acrylamide and the 1-acryloyl-4-methyl piperazine qauternary ammonium salt.

The following Examples describe in detail solution polymerizations in which certain copolymers of 1-acryloyl-4-methyl piperazine quaternary ammonium salt and acrylamide are prepared. In each of these Examples the polymerizations were carried out in a standard laboratory resin reactor, under a nitrogen blanket, with continuous agitation and temperature control, with a nitrogen purge of reaction mixture before initiation.

EXAMPLE 4

To the reactor were charged 5 ml. of a 1% sodium formate water solution, 2.5 ml. of a 2% water solution of Versene (a chelating agent), 6.04 grams of a 50 wt. percent solution of a dimethyl sulfate quaternary ammonium salt of 1-acryloyl-4-methyl piperazine in water (the preparation of which is described above in Example 1), 14.85 grams of a 46.4 wt. percent acrylamide solution in water, and 167.5 grams of dilution water. All water charged, including that of the various water solutions, was deionized water. The reaction was initiated by the charge of 0.03 grams of V-50 (Wako) as 4 ml. of a solution containing 0.12 grams of V-50 in 16 ml. water. At the time of initiation, the reaction mixture was heated to 45° C., at which temperature it was held for a 5 hour reaction time. The reaction was then stopped and the mixture cooled to room temperature.

The reaction provided a polymeric solution of 4.6 wt. percent solids. Gas phase chromatographic analysis of residual monomer showed the polymerization to be 95.2% completed. The resultant polymer contained 91 mole percent acrylamide and 9 mole percent of the dimethyl sulfate quaternary ammonium salt of 1-acryloyl-4-methyl piperazine and had an intrinsic viscosity of 4.02.

EXAMPLE 5

The procedure and techniques described in Example 4 were followed except the charge was: 2.5 ml. of a 2% Versene water solution; 9.90 grams of a 50 wt. percent water solution of dimethyl sulfate quaternary ammonium salt of 1-acryloyl-4-methyl piperazine; 10.86 grams of a 46.4 wt. percent water solution of acrylamide; and 172.74 grams water of dilution. The reaction was initiated with 0.03 grams of V-50, added as 4 ml. of a 0.12 grams in 16 ml. of water solution. At initiation, the reaction mixture had been heated to 45° C., and then was held at such temperature for a 5.25 hour reaction time.

The resultant polymeric solution contained 5.0% solids. Gas phase chromatographic residual monomer analysis showed the polymerization to be 98.4% completed. The resultant polymer contained 20 mole percent of the quaternary ammonium salt and 80 mole percent of the acrylamide, and had an intrinsic viscosity of 3.9.

EXAMPLE 6

To the reactor were charged 1 ml. of a 2% water solution of Versene, 12.56 grams of a 50 wt. percent solution of a dimethyl sulfate quaternary ammonium salt of 1-acryloyl-4-methyl piperazine in water, 8.02 grams of a 46.4 wt. percent acrylamide solution in water, and 174.65 grams of dilution water. All water charged, including that of the various water solutions, was deionized water. The reaction was initiated by a charge of 0.03 grams of V-50 (Wako) as 1 ml. of a solution containing 0.12 grams of V-50 in 4 ml. water. The reaction procedure and techniques described in Example above were followed.

The reaction provided a polymeric solution of 5.0 wt. percent solids. Gas phase chromatographic analysis of residual monomer showed the polymerization to be completed. The resultant polymer contained 70 mole percent acrylamide and 30 mole percent of the dimethyl sulfate quaternary ammonium salt of 1-acryloyl-4-methyl piperazine and had an intrinsic viscosity of 5.57.

The following Examples describe in detail solution polymerizations in which certain homopolymers of 1-acryloyl-4-methyl piperazine quaternary ammonium salt are prepared. In each of these Examples the polymerizations were carried out in a standard laboratory resin reactor, under a nitrogen blanket, with continuous agitation and temperature control, using deionized water throughout, and purging the reaction mixture with nitrogen before initiation.

EXAMPLE 7

To the reactor were charged 2 ml. of a 2% water solution of Versene, 20 grams of a 50 wt. percent solution of a dimethyl sulfate quaternary ammonium salt of 1-acryloyl-4-methyl piperazine in water, 70.8 grams of dilution water, and 0.7 grams ammonium persulfate in 5 ml. water. At the time of initiation, the reaction mixture had been heated to 60° C., and then was held at 60° to 65° C. for a 3 hour reaction time. The reaction mixture was then heated to 70° C. and held at this temperature of 1 hour. The reaction provided a polymer solution of 10.15 wt. percent solids. GC analysis of residual monomer showed the polymerization to be 99.9% completed. The resultant polymer had an intrinsic viscosity of 0.23.

EXAMPLE 8

The procedure and techniques described in Example 7 were followed except the charge was: 1 ml. of a 2% Versene water solution; 20 grams of a 50 wt. percent water solution of dimethyl sulfate quaternary ammonium salt of 1-acryloyl-4-methyl piperazine; 0.25 grams of 0.25% sodium formate; and 74.75 grams water of dilution. The reaction was initiated with 0.03 grams of V-50, added as 4 ml. of a 0.12 grams in 16 ml. water solution. At initiation, the reaction mixture had been heated to 42° C., and then was held at 45° C. for a 5 hour reaction time.

The resultant polymer solution contained 9.97% solids. The polymer had an intrinsic viscosity of 1.78.

EXAMPLE 9

The polymerization of the immediately preceding Example 8 was repeated except the charge of the 0.25% sodium formate solution was increased to 1.6 grams and the water of dilution decreased to 73.5 grams. The resultant polymer had an intrinsic viscosity of 1.37. The solution solids were 10%.

EXAMPLE 10

The reaction procedures and techniques of the preceding two Examples 8 and 9 were followed using the following charge: 0.5 ml of 2% Versene; 10 grams of the 1-acryloyl-4-methyl piperazine dimethyl sulfate quaternary ammonium salt; 2.5 grams of 0.25% sodium formate; and 36.75 grams of water of dilution. The reaction was initiated at 45° C. with 0.3 grams of V-50 in 4 ml. water, and held at this temperature for a 5 hour and 20 minute reaction time. The resultant polymer had an intrinsic viscosity of 0.7, and the polymer solution contained 9.3 wt. percent solids.

EXAMPLE 11

Using the techniques of the preceding examples, a homopolymer of 1-acryloyl-4-methyl piperazine dimethyl sulfate quaternary ammonium salt having an intrinsic viscosity of 2.55 was prepared as a 9.38 wt. percent solids water solution.

The homopolymers and copolymers of the quaternary ammonium salts of 1-acryloyl-4-methyl piperazine can also be made by methods which utilize the technique of polymerization of water-soluble vinyl monomers in the form of water-in-oil emulsions. This technique is described in Vanderhoff U.S. Pat. No. 3,284,393, the disclosures of which are incorporated herein by reference.

The following Example 12 illustrates such oil-in-water polymerization technique for the preparation of a copolymer containing 1-acryloyl-4-methyl piperazine and acrylamide.

EXAMPLE 12

The oil phase comprised the following: 32.5 grams LOPS (a low odor parafinic solvent); 0.62 grams TWEEN 61 (a low polyethoxylated sorbitan monostearate); and 1.87 grams SPAN 80 (a 20 unit ethoxylated sorbitan monooleate). The aqueous phase comprised the following: 16.86 grams of 1-acryloyl-4-methyl piperazine; 39.08 grams of a 46.4% water solution of acrylamide; 26.94 grams water, and 1 ml. of a 2% Versene solution. The polymerization was carried out in a resin reactor, under a blanket of nitrogen, with continuous agitation and temperature control. Deionized water was used throughout. The reaction was initiated with 0.07 grams of Vazo 64 in 4 ml. DMF. The resultant polymer had an intrinsic viscosity of 7.1, and about 30 mole percent of the piperazine. By GC residual monomer analysis the polymerization was determined to have been about 88% completed. The latex contained 25% solids.

Other suitable polymers may contain the 1-acryloyl-4-methyl piperazine polymerized together with suitable nonionic vinyl addition monomers such as: methacrylamide, acrylonitrile, N-vinyl pyrrolidinone, vinyl acetate, lower alkyl acrylates, lower alkyl methacrylates, lower alkyl ethacrylates, styrene and the like. Suitable vinyl addition cationic co-monomers include: dimethylaminoethylacrylate, quaternary ammonium salts of dimethylaminoethylacrylate, dimethylaminoethylmethacrylate, quaternary ammonium salts of dimethylaminoethylmethacrylate, diallyldimethylammonium chloride, methacrylamidopropyltrimethyl ammonium chloride, vinyl pyridine, N,N-dimethylaminomethylacrylamide, N,N-dimethylaminomethylmethacrylamide, N,N-dimethylaminomethylacrylamide quaternary ammonium salts, and the like. Suitable vinyl addition anionic co-monomers include: acrylic acid, methacrylic acid, itaconic acid, maleic anhydride, acrylamidomethylpropanesulfonic acid, and the like.

Such polymers containing the 1-acryloyl-4-methyl piperazine monomer may contain from about 1 to about 99 mole percent of the other vinyl addition co-monomer or co-monomers. In preferred embodiment, such polymeric compositions will contain from about 1 to about 70 mole percent, and more preferably from about 2 to about 50 mole percent, of the other vinyl addition co-monomer or co-monomers. Particularly useful polymers are those derived from the polymerization of the 1-acryloyl-4-methyl piperazine together with acrylamide. Such copolymers have been found extremely active in oily water clarification processes. Such polymeric compositions may contain from about 1 to about 99 mole percent of acrylamide. In preferred embodiment, such polymeric compositions contain from about 50 to about 95 mole percent acrylamide, and more preferably from about 65 to about 95 mole percent acrylamide. Such polymers, of course, may contain other vinyl addition co-monomers in addition to the acrylamide and the 1-acryloyl-4-methyl piperazine.

Emulsion breaking, the resolution of an emulsion, such as an oil-in-water emulsion, into separate continuous oil and water phases, is an important industrial application, often associated with the treatment of industrial waters containing such emulsion as an undesirable contaminant. The automotive industry commonly uses paint emulsions. In refineries and steel mills waters containing emulsified oil are often formed. Oil field produced waters can contain both dispersed oil and solids.

Polymers of the quaternary ammonium salts of 1-acryloyl-4-methyl piperazine, including the homopolymer thereof and polymers derived from the polymerization of the quaternary ammonium salt together with other suitable vinyl addition monomers, have been found extremely active in emulsion breaking applications, as shown below in Examples 13 to 17.

EXAMPLES 13 TO 17

A number of the polymers prepared in preceding examples demonstrated oil-in-water emulsion breaking activities at low dosages based on active polymer in in a series of comparative tests, as follows. The polymer was added to an oil-in-water emulsion which was then agitated for a 6 minute period. Then 150 ppm alum was added and agitation, at a lower speed, was continued for 3 minutes, followed by the addition of 2 ppm of a commercial anionic flocculant with a further lower speed of agitation continued for 1 minute. Effectiveness was determined by the turbidity of the test mixture after it had been allowed to settle for 30 minutes after agitation ceased.

Set out in Table I below are the dosage ranges at which such polymers were found effective as emulsion breakers in this test. These dosage ranges are at least on the same level with, and in some instances lower than, that of materials presently in commercial use in emulsion breaking applications.

TABLE I

| Example # | Polymer Example No. of Preparation | Dosage Range as 100% Active Polymer |
|---|---|---|
| 13 | Example 4 | 54 to 110 ppm |
| 14 | Example 5 | 70 to 90 ppm |
| 15 | Example 6 | 70 to 90 ppm |
| 16 | Example 7 | 120 to 130 ppm |
| 17 | Example 10 | 100 to 110 ppm |

In oil field water clarification the removal of both dispersed oil and solids is often required. In such clarification processes copolymers of 1-acryloyl-4-methyl piperazine with other vinyl addition monomers, particularly acrylamide, have surprisingly shown activity surpassing some materials in present commercial use for such processes, as shown below in Example 18.

EXAMPLE 18

In the following Bench Wemco Coagulation Test, materials were tested at various concentrations for one minute at 170 rpm in a small Wemco unit for clarification of oil field type waters containing dispersed solids and oil. The test samples were allowed to sit for 10 seconds after the one minute agitation period and then the percent light transmittance therethrough was measured on a photometer. A copolymer of 1-acryloyl-4-methyl piperazine and acrylamide, whose preparation is described above in Example 12, having about 30 mole percent of the piperazine and 70 mole percent of the acrylamide, was tested and found to be of superior activity at various typical dosage levels when compared to commercial products for such applications. Such commercial products were of the high molecular weight dimethylaminoethylmethacrylate dimethyl sulfate quaternary ammonium salt and acrylamide copolymer type. This comparative data is set out below in Table II.

TABLE II

| Dosage as 100% active polymer | Percent Transmission | | | |
|---|---|---|---|---|
| | 1-acryloyl-4-methyl piperazine | Commercial Products | | |
| | | #1 | #2 | #3 |
| 1.0 ppm | 73 | 55 | 38 | 43 |
| 2.0 ppm | 90 | 70 | 48 | 48 |
| 3.0 ppm | 95 | 80 | 58 | 53 |

In the above discussions and examples, all percentages given, unless specified otherwise, are weight percentages.

Industrial Applicability of the Invention

The present invention is applicable to the oily water clarification and emulsion breaking applications of many industries, including without limitation the oil production industries, the automotive industries, the steel production industries, and the paper and pulp industries.

We claim:

1. A process for clarifying dispersed oil containing water comprising:
   the addition of a polymer of a quaternary ammonium salt of 1-acryloyl-4-methyl piperazine to water containing dispersed oil in an amount effective to clarify said water by elimination of said dispersed oil.

2. The process of claim 1 wherein said polymer is a copolymer of 1-acryloyl-4-methyl piperazine quaternary ammonium salt and another vinyl addition monomer, which copolymer contains between 1 and 99 mole percent of the 1-acryloyl-4-methyl piperazine quaternary ammonium salt.

3. The process of claim 2 wherein said vinyl addition monomer is acrylamide.

* * * * *

UNITED STATES PATENT AND TRADEMARK OFFICE
CERTIFICATE OF CORRECTION

PATENT NO. : 4,802,992

DATED : February 7, 1989

INVENTOR(S) : Dodd W. Fong and Ann M. Halverson

It is certified that error appears in the above-identified patent and that said Letters Patent is hereby corrected as shown below:

In the Abstract, line 2, cancel "surfate" and substitute therefor -- sulfate --.

Col. 2, line 24, cancel "piperaine" and substitute therefor -- piperazine --.

Signed and Sealed this

Tenth Day of October, 1989

Attest:

DONALD J. QUIGG

Attesting Officer

Commissioner of Patents and Trademarks